(12) United States Patent
Newman et al.

(10) Patent No.: US 10,551,374 B2
(45) Date of Patent: Feb. 4, 2020

(54) METHOD AND DEVICE FOR DETECTING AN ANALYTE USING PHASE LAG

(75) Inventors: David Newman, Teignmouth (GB); Raphael Matelon, Exeter (GB)

(73) Assignee: COTTON MOUTON DIAGNOSTICS LIMITED, Gwent (GB)

( * ) Notice: Subject to any disclaimer, the term of this patent is extended or adjusted under 35 U.S.C. 154(b) by 1328 days.

(21) Appl. No.: 14/241,534

(22) PCT Filed: Sep. 3, 2012

(86) PCT No.: PCT/GB2012/052160
§ 371 (c)(1),
(2), (4) Date: Sep. 2, 2014

(87) PCT Pub. No.: WO2013/030601
PCT Pub. Date: Mar. 7, 2013

(65) Prior Publication Data
US 2015/0125873 A1    May 7, 2015

(30) Foreign Application Priority Data

Sep. 1, 2011 (GB) .................................. 1115120.6

(51) Int. Cl.
G01N 33/543 (2006.01)
(52) U.S. Cl.
CPC .............................. G01N 33/54326 (2013.01)
(58) Field of Classification Search
CPC .. G01N 27/745; G01N 21/1717; G01N 21/21; G01N 33/54326; G01N 2021/1727; G01N 2021/218; H01F 1/0054; B22F 2999/00
See application file for complete search history.

(56) References Cited

U.S. PATENT DOCUMENTS

| | | | | |
|---|---|---|---|---|
| 6,470,220 B1* | 10/2002 | Kraus, Jr. | .......... | A61K 41/0052 600/12 |
| 2004/0058458 A1 | 3/2004 | Anker et al. | | |
| 2005/0025969 A1* | 2/2005 | Berning | ................ | B22F 1/0018 428/403 |
| 2006/0008924 A1* | 1/2006 | Anker | .................. | G01N 33/587 436/526 |
| 2007/0164271 A1* | 7/2007 | Wait, Jr. | ............. | A61K 41/0028 257/25 |
| 2007/0172890 A1* | 7/2007 | Prins | ........................ | B82Y 5/00 435/7.1 |
| 2008/0011977 A1* | 1/2008 | Atwood | .................. | B82Y 15/00 252/62.51 R |
| 2008/0129286 A1* | 6/2008 | Kahlman | ............... | B82Y 25/00 324/225 |
| 2008/0220411 A1* | 9/2008 | McNaughton | ... | G01N 33/54313 435/5 |
| 2009/0085557 A1* | 4/2009 | Krozer | .................. | G01R 33/12 324/201 |
| 2010/0003197 A1* | 1/2010 | Bikram | .................. | A61K 33/24 424/9.323 |
| 2010/0105026 A1* | 4/2010 | Bruckl | .................... | B82Y 15/00 435/5 |
| 2010/0303716 A1* | 12/2010 | Jin | ..................... | A61M 37/0092 424/1.11 |
| 2011/0156701 A1* | 6/2011 | Ranzoni | ........... | G01N 33/54333 324/244 |
| 2011/0206619 A1* | 8/2011 | Mahmoudi | ............ | A61K 49/00 424/9.323 |
| 2012/0119727 A1* | 5/2012 | Prins | .................... | G01N 27/745 324/204 |
| 2012/0251392 A1* | 10/2012 | Sandhu | .............. | G01N 21/1717 422/69 |
| 2015/0038347 A1* | 2/2015 | Johnson | ............... | C12Q 1/6825 506/9 |

FOREIGN PATENT DOCUMENTS

| | | |
|---|---|---|
| WO | 2005111596 A1 | 11/2005 |
| WO | 2008056171 A2 | 5/2008 |
| WO | 2008124853 A1 | 10/2008 |
| WO | 2011049044 A1 | 4/2011 |

OTHER PUBLICATIONS

International Search Report and Written Opinion dated Feb. 13, 2013 in connection with PCT/GB2012/052160.
Search Report dated Dec. 16, 2011 in connection with GB application No. 1115120.6.
Stanciu L. et al: "Magnetic particle-based hybrid platforms for bioanalytical sensors", Sensors, vol. 9, No. 4, 2009; pp. 2976-2999; XP55052167.
Mens P.F. et al: "Laboratory evaluation on the sensitivity and specificity of a novel and rapid detection method for malaria diagnosis based on magneto-optical technology (MOT)", MALRIA J., vol. 9, No. 1, Jul. 19, 2010; p. 207; XP021077366.
Schrittwieser et al. "Homogeneous biosensor based on optical detection of the rotational dynamics of anisotropic nanoparticles" Proc. Eurosensors XXIV, Sep. 5-8, 2010, pp. 1107-1110.

* cited by examiner

Primary Examiner — Ann Y Lam
(74) Attorney, Agent, or Firm — Quarles & Brady LLP

(57) ABSTRACT

According to the invention there is provided a method of detecting an analyte including the steps of: i) providing a sample which contains the analyte and magnetic nanoparticles, in which the magnetic nanoparticles include a magnetic body portion which acts as a signalling vector and at least one receptor moiety attached to the body portion for binding to the analyte; ii) applying a magnetic field across at least a portion of the sample to orient the magnetic nanoparticles with respect to the applied magnetic field; iii) introducing electromagnetic radiation into the sample; iv) detecting a physical property which varies in dependence on the orientation of the magnetic nanoparticles with respect to the applied magnetic field, wherein the physical property is associated with the interaction of the electromagnetic radiation with the magnetic body portion which thereby acts as a signalling vector; and v) correlating the detected physical property with the presence of the analyte.

15 Claims, 4 Drawing Sheets

METHOD AND DEVICE FOR DETECTING AN ANALYTE USING PHASE LAG

CROSS-REFERENCE TO RELATED APPLICATIONS

This application represents the national stage entry of PCT International Application No. PCT/GB2012/052160 filed Sep. 3, 2012, which claims priority to Great Britain Patent Application 1115120.6 filed Sep. 1, 2011, the disclosures of which are hereby incorporated by reference in their entirety for all purposes.

This invention relates to a method and device for detecting an analyte, and to certain particles which may be used in the method. The invention relates also to an associated kit. Particular, but by no means exclusive, reference is made to the detection of bio-molecules or biological material.

There is intense interest in the provision of diagnostic kits based on antigen tagged signalling vectors. However, there are drawbacks associated with current technologies, in particular with regard to the time taken to analyse any significant volume of analyte. More particularly, it is normally essential to remove, by some form of pre-processing, all excess signals vectors prior to performing the actual assay. The omission of a pre-processing step would open the possibility of assaying significant sample volumes with a concomitant enhancement in the ability to detect low levels of disease. This is not possible with most current technologies. For example, technologies which involve tagged magnetic beads and the measurement of a magnetic response are constrained to operating the micro-fluidic regime by both the sensing methodology and the need for pre-processing. It is therefore either impossible or extremely time consuming to analyse any significant volume of analyte in these and similar systems.

The use of magnetic field modulation as a means of improving signal to noise in simple fluorescent tagging systems has been disclosed by Anker et al (1). In this approach, magnetic particles are tagged with fluorescent dyes. The magnetic particles are constrained so that the fluorescent dyes emit electromagnetic radiation in only one direction, and a "lighthouse" signalling system is created by using magnetic fields to rotate the magnetic particles. This is a relatively complex system to implement.

The present invention, in at least some of its embodiments, addresses the above mentioned problems and desires.

According to a first aspect of the invention, there is provided a method of detecting an analyte including steps of:

i) providing a sample which contains the analyte and magnetic nanoparticles, in which the magnetic nanoparticles include a magnetic body portion which acts as a signalling vector and at least one receptor moiety attached to the body portion for binding to the analyte;

ii) applying a magnetic field across at least a portion of the sample to orient the magnetic nanoparticles with respect to the applied magnetic field;

iii) introducing electromagnetic radiation into the sample;

iv) detecting a physical property which varies in dependence on the orientation of the magnetic nanoparticles with respect to the applied magnetic field, wherein the physical property is associated with the interaction of the electromagnetic radiation with the magnetic body portion which thereby acts as a signalling vector; and v) correlating the detected physical property with the presence of the analyte.

Preferably the electromagnetic radiation propagates through the sample along an axis which is transverse to the direction of the applied magnetic field.

Advantageously, the magnitude and/or the direction of the applied magnetic field is varied, and a dependence of the physical property on the variation of the applied magnetic field is detected. In some preferred embodiments, a dynamic response of the physical property to the variation of the applied magnetic field is detected as a function of time, or a quantity functionally related thereto, such as frequency, and the dynamic response is correlated with the presence of the analyte. The phase of the physical property with respect to the variation of the applied magnetic field may be detected.

The direction of the applied magnetic field may be varied by rotating said direction about the sample at a desired rotational frequency, and a dependence of the physical property on the rotational frequency may be detected. The phase of the physical property with respect to the rotational frequency may be detected. Typically, the physical property exhibits a characteristic phase lag, at least at higher rotational frequencies where the magnetic nanoparticles cannot follow the rotating magnetic field. The rotational frequency may be varied, in which instance the response (such as the phase lag) of the physical property as a function of rotational frequency may be detected. For example, the component of the response which is in phase with the applied magnetic field may be detected.

The physical property detected may be the transmission of the electromagnetic radiation through the sample.

Alternatively, the physical property detected may be fluorescence emitted from the magnetic body portion.

Advantageously, the electromagnetic radiation is polarised.

Preferably, the magnetic body portion includes a magnetic core and surface coating.

The surface coating can be used to provide one or more advantageous properties. For example, the surface coating can be selected so as to improve biocompatibility or to reduce agglomeration and improve dispersion of the nanoparticles in the sample. The surface coating may be selected so as to enhance the detection process. For example, the surface coating and the electromagnetic radiation may interact to produce plasmons, thereby enhancing the detection of the physical property.

The detected physical property may be fluorescence emitted from the surface coating.

Preferably, the surface coating is gold. A gold surface coating can provide all of the advantages described above. Silver may be used instead of the surface coating, and this can also produce a plasmonic response. Silver is generally less preferred for use in biological systems, although it can be usefully employed in the detection of analytes in non-biological systems.

The electromagnetic radiation can be of any suitable wavelength. Typically, the electromagnetic radiation is in the visible or near infra-red regions of the spectrum. Thus, the electromagnetic radiation may be in the range 400 to 2,500 nm. Advantageously, the analyte is a bio-molecule or biological material. The bio-molecule or biological material may be a biopolymer, cellular material or other antigens. Bio-molecules which might be detected include nucleic acids such as DNA and RNA, and proteins. The method may be employed as part of an assay technique, such as an immuno assay. The sample may comprise any suitable or desirable medium containing the bio-molecule or biological material, including a bodily fluid such as blood or blood serum. In instances where blood or blood serum is analysed, electromagnetic radiation of a frequency at which the blood or blood serum is reasonably transparent is typically utilised, for example electromagnetic radiation in wavelength range 400-1,300 nm.

Other analytes may be detected, such as small molecules. Organic molecules, inorganic molecules, acids and ions may be detected. Examples of classes of analyte such as might be detected using the invention include drugs, toxins, other hazardous chemicals, etc.

Conveniently, the method is used for detecting a plurality of analytes, in which: the sample contains a plurality of different kinds of magnetic nanoparticles, each of said kinds binding to a different analyte by virtue of having a different receptor moiety; and the detected physical property associated with each of said kinds when bound to its associated analyte is different, allowing the detected physical property to be correlated with the presence of the associated analyte.

According to a second aspect of the invention there is provided a device for detecting an analyte in a sample which contains the analyte and magnetic nanoparticles of the type including a magnetic body portion which acts as a signalling vector and at least one receptor moiety attached to the body portion for binding to the analyte, the device including:

a magnetic field production device for applying a magnetic field across at least a portion of the sample;

a source of electromagnetic radiation which is introduced into the sample;

a detector for detecting a physical property which varies in dependence on the orientation of the magnetic nanoparticles with respect to the applied magnetic field, wherein the physical property is associated with the interaction of the electromagnetic radiation with the magnetic body portion, which thereby acts as a signalling vector; and a correlator for correlating the detected physical property with the presence of the analyte The device may be configured so that the magnitude and/or the direction of the applied magnetic field is controllably variable. In these embodiments, the magnetic field production device may include an electromagnet. Alternatively, the magnetic field production device may be a permanent magnet having a movement device for moving the permanent magnet with respect to the sample. For example, the movement device may rotate the permanent magnet about the sample at a desired rotational frequency. The rotational frequency may be controllably variable.

Preferably, the electromagnetic radiation propagates into the sample along an axis which is transverse to the direction of the applied magnetic field.

The detector may detect electromagnetic radiation transmitted through the sample.

Alternatively, the detector may detect fluorescence emitted from the magnetic body portion.

According to a third aspect of the invention there is provided a kit for detecting an analyte including:

a device according to the second aspect of the invention; and a supply of magnetic nanoparticles, the magnetic nanoparticles including a magnetic body portion which acts as a signalling vector and at least one receptor moiety attached to the body portion for binding to the analyte.

According to a fourth aspect of the invention there is provided a magnetic nanoparticle including a magnetic body portion which acts as a signalling vector, and at least one receptor moiety attached to the body portion for binding to the analyte. Typically, the body portion is paramagnetic or superparamagnetic. In this way, unwanted clumping of nanoparticles can be minimised.

Preferably, the magnetic body portion includes a magnetic core and a surface coating. The surface coating may be formed from a metal such as gold or silver. Gold is particularly preferred.

Advantageously, the magnetic nanoparticle is elongate in shape. Rod-shaped magnetic nanoparticles may be used.

Typically, the magnetic nanoparticle is in the size range 300 to 1,000 nm. This enables detection to be performed in the visible or near infra-red regions of the electromagnetic spectrum.

The magnetic body portion may include an iron oxide, nickel and/or cobalt. Magnetite may be used.

The receptor moiety may be any convenient type. Conveniently, the receptor moiety may be of a type which binds to a bio-molecule or biological material. The receptor moiety may be an antibody such as an immunoglobulin.

The receptor moiety may be attached to the body portion using techniques which are well known to the skilled reader. References 6 and 10-15, the entire contents of all of which are herein incorporated by reference, are examples of publications which describe how to functionalise magnetic body portions in order attach a desired receptor moiety. Reference 6 reviews the biofunctionalisation of magnetic nanoparticles, including biofunctionalisation of gold and iron oxide surfaces. References 10-15 described biofunctionalisation of nanoparticles having gold surfaces. The skilled reader will appreciate that various schemes may be employed to attach the receptor moiety to the body portion. The receptor moiety may be attached via covalent bonding or via surface absorption, for example adsorption onto a polymeric or other suitable layer deposited on the magnetic body portion.

Whilst the invention has been described above, it extends to any inventive combination of the features set out above, or in the following description, drawings or claims. For example, features of one aspect of the invention may be applied or utilised in other aspects of the invention.

Devices and methods in accordance with the invention will now be described, by way of example only, with reference to the accompanying drawings, in which:—

Figure 3:
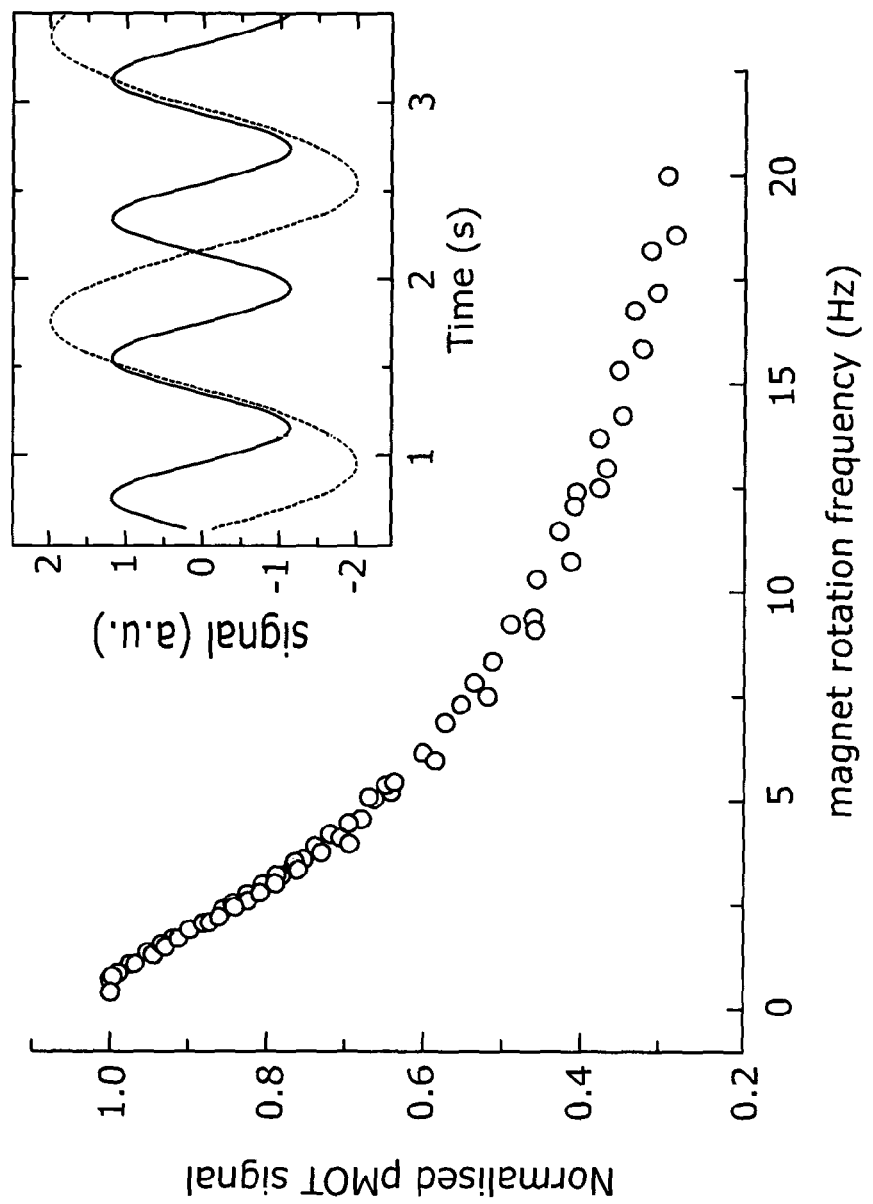
Figure 4:
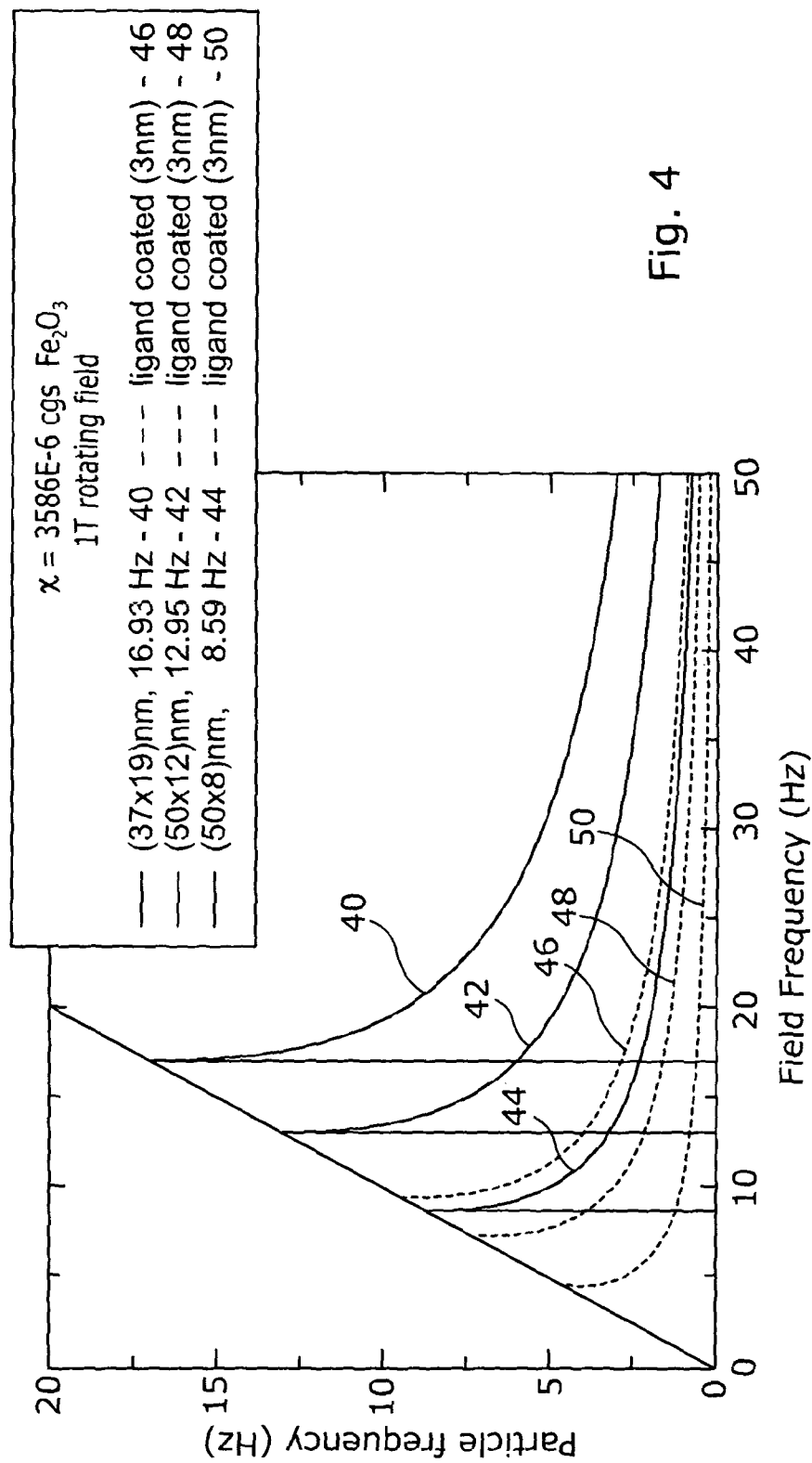

FIG. 3 shows in the main graph the component of a magneto-optic signal in phase with an applied magnetic field as a function of the rotational frequency of the magnetic field, and in the inset magneto-optic response as a function of the rotational frequency of the applied magnetic field; and FIG. 4 shows the dynamic response of nanorods of different dimensions as a graph of nanoparticle frequency vs the frequency of the applied magnetic field.

Figure 1:
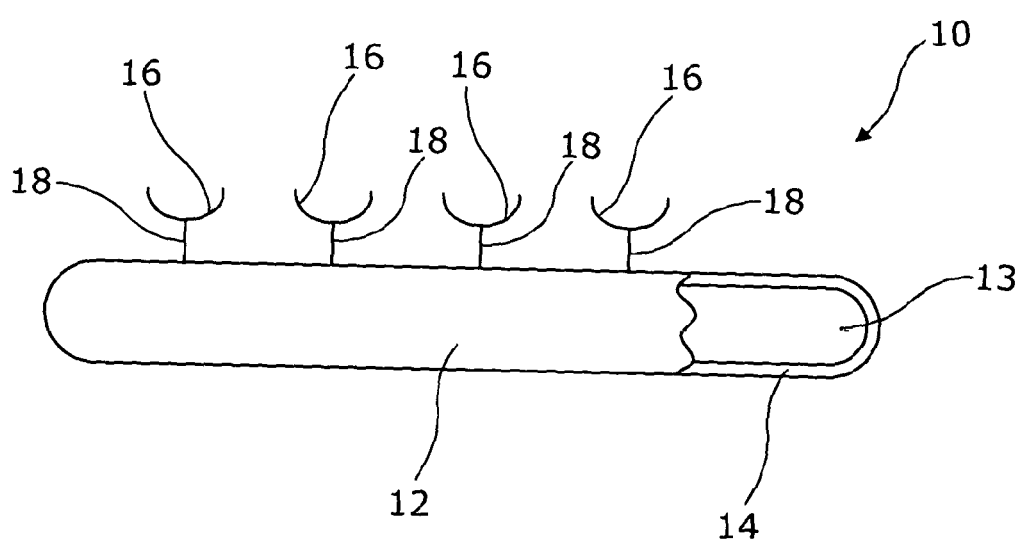
FIG. 1 shows a magnetic nanoparticle of the invention.

FIG. 1 shows a magnetic nanoparticle, depicted generally at 10. The magnetic nanoparticle 10 comprises a magnetic elongate body portion 12 which is formed from a magnetic material 13 and a surface coating 14. Receptor moieties 16 are present on the surface coating; the receptor moieties may be connected to the surface coating by suitable molecular linkages 18. The magnetic nanoparticle may be provided in a variety of elongate forms, but a particularly preferred configuration is the rod-shaped configuration shown in FIG. 1. Such forms are comparable to haemozoin structures produced by the malaria parasite, and which the present inventors have demonstrated to give rise to a measurable magneto-optic effect (International Patent Application No. PCT/GB2007/004300; references 2-5, the entire contents of all of which are herein incorporated by reference). The appropriately shaped magnetic body portion 12 can be produced by known synthesis routes (6, 7, the entire contents of both of which are herein incorporated by reference), and it is readily possible to control the composition, size and shape of these body portions. In fact, a wide range of products is available commercially which enables nanoparticles to be designed with precise dimensions and magnetic susceptibilities. It is possible to provide magnetic nanoparticles which do not have a surface coating 14, in which the receptor moiety 16 are directly coupled to the body portion 12 by the molecular linkages 18. However, embodiments which utilise the surface coating 14 are preferred. The surface coating 14 can confer a number of benefits. For example, many as-produced magnetic nanoparticles are not optimally biocompatible and may tend to agglomerate unless extremely finely dispersed. The provision of a suitable surface coating 14 can overcome both of these potential problems. It is particularly preferred to utilise a gold surface coating. Methodologies for producing suitable gold surface coatings are known (8, the entire contents of which are herein incorporated by reference). Further advantages associated with the gold coating is that it favours the binding of antigens to the surface, and it permits a favourable detection mechanism. This detection mechanism is plasmon enhancement, i.e., the resonant excitation of plasmons in localised orbits around the particles. This is a highly selective process which can lead to a massive increase in optical absorption of the nanoparticles when the wavelength of the exciting radiation is optimally matched to the dimensions of the plasmon orbits possible around the particle, and its electric vector is appropriately aligned to excite that orbit. If rod-shaped nanoparticles of the type shown in FIG. 1 of a particular length are irradiated with the precise wavelength necessary to excite plasmons around their long axis then, provided the long axis is also aligned with the electric vector of the incident radiation, extremely substantial optical absorption will be achieved as plasmons are optically excited but decay thermally. Conversely, if the long axis of the nanoparticles is aligned orthogonally to the electric vector of the incident radiation, then the precise conditions essential for plasmon generation are broken, and minimal optical absorption is observed. Therefore, under the action of the applied magnetic field, a dispersion of rod-shaped nanoparticles in a fluid can exhibit a plasmon augmented magneto-optic response. It is anticipated that a plasmon augmented extraordinary Cotton-Mouton effect can be observed which is potentially one to three orders of magnitude greater than that exhibited by haemozoin.

Plasmon augmented absorption measurements can be made by detecting light transmitted through the sample with magnetic field modulation. Alternatively, fluorescence emitted from the surface coating can be used in combination with magnetic field modulation. This may provide further enhancements in sensitivity and specificity. Plasmon mediation has been found to enhance the quantum efficiency of luminescence from gold nano-rods a million fold in comparison to the bulk metal (9) and a similarly favourable behaviour, together with greatly improved wavelength selectivity, was observed when this phenomenon was exploited in conjunction with two photon luminescence (7).

Figure 2A:
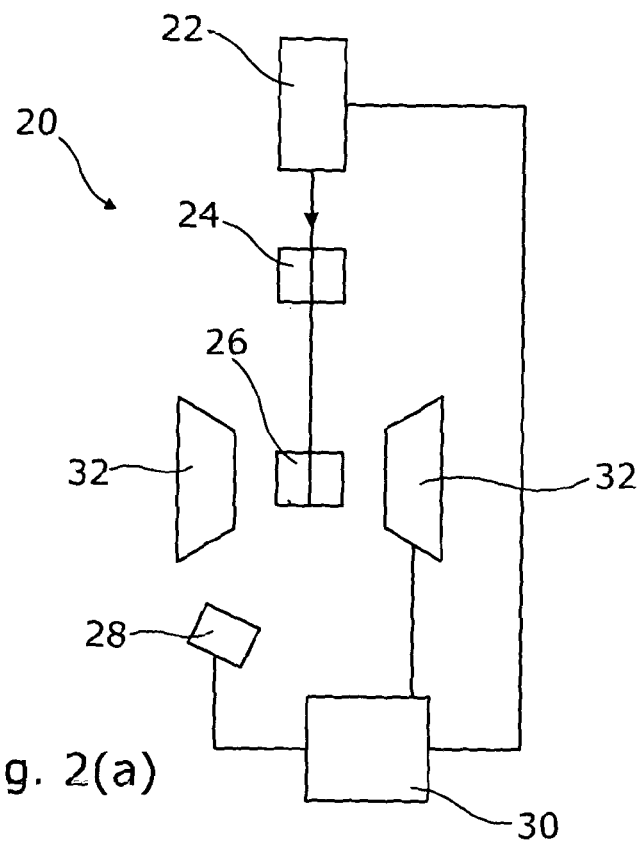
FIG. 2 shows detection arrays utilising (a) fluorescence detection and (b) absorption detection.

FIG. 2 shows detection arrangements for detecting an analyte using magnetic nanoparticles of the type depicted in FIG. 1. FIG. 2(a) shows a first arrangement, depicted generally at 20, for performing fluorescence measurements. The arrangement 20 comprises a light source 22 for producing light of a desired wavelength or range of wavelengths, the output of which passes through a polariser 24 before entering a suitable cell 26 containing the sample under analysis. The sample is a liquid sample containing the analyte of interest and the magnetic nanoparticles. Fluorescence emanating from the sample is detected by a fluorescence detector 28 and the output of the fluorescence detector 28 is analysed by a suitable analysis device 30 such as a computer or other microprocessor containing device. The arrangement 20 further comprises a magnetic field production device 32. The analysis device 30 may also function as a controller, or a physically separate controller device may be utilised. The controller can be used to control the operation of the light source 22 and/or the magnetic field production device 32. It is also possible for the controller to control the operation of the polariser 24, such as in embodiments in which polarisation modulation is performed or polarisation state dependent variations in the fluorescence are detected. However, it is preferred that the detection is achieved using magnetic field modulation. This can be achieved by employing an electromagnet as the magnetic field production device 32 and operating the electromagnet so as to modulate the strength of the magnetic field applied across the sample in the cell 26. Alternatively, an arrangement can be utilised in which a permanent magnet applies the magnetic field across the sample in the cell 26. The permanent magnet can be moved by a suitable mechanical arrangement, for example utilising one or more actuators which are controlled by the controller thereby modulating the direction of the applied magnetic field. Rotation of the permanent magnet around the sample is possible.

Figure 2B:
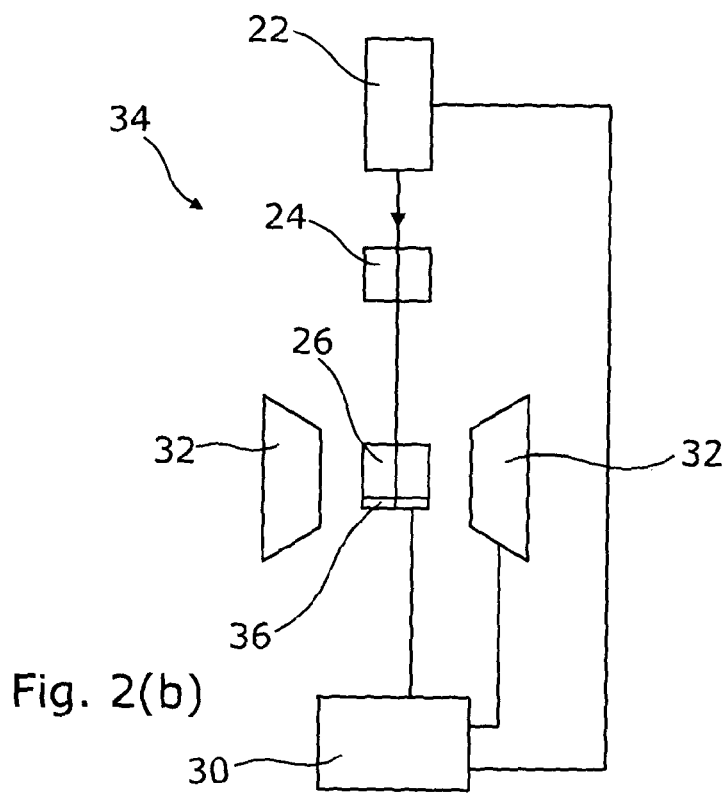

FIG. 2(b) shows a detection arrangement, depicted generally at 34, in which transmission measurements are made. The transmission arrangement of FIG. 2(b) shares numerous features with the fluorescence arrangement of FIG. 2(a), and common numerals are used to denote such shared features. The principal difference is that a suitable photo-detector 36 is positioned at or near to a rear face of the cell 26 so that light from the light source 22 which is transmitted through the cell 26 is detected by the photo-detector 36. The output of the photo-detector 36 is fed into the analysis device 30, and absorption measurements can therefore be obtained. As described with reference to FIG. 2(a), the analysis device 30 or a separate controller can be used to control the operation of the light source 22 and the magnet 32 so as to provide magnetic field modulation detection, although it is also possible to control the operation of the polariser 24.

The nature of the nanoparticles can be selected and produced in accordance with known synthesis routes (6, 7). In particular, the length and other dimensions of the nanoparticles together with the magnetic material that the nanoparticles are formed from can be varied in order to provide a desired response. In embodiments in which a blood or blood serum sample is utilised it is preferred that the nanoparticles are selected so that they may be interrogated in the wavelength range 400-1300 nm where blood and blood serum is reasonably transparent. The response of a given class of nanoparticles can be determined in a straightforward manner by using a broadband light source 22 together with some form of variable wavelength selection, such as appropriate filters or a monochromator. Alternatively, one or more tunable laser sources might be used.

The presence of an analyte is detected when the analyte attaches to the receptor moieties on the magnetic nanoparticles. This gives rises to a perturbation in the response characteristic of the magnetic nanoparticles which is detected and is correlated with the coupling of the analyte to the receptor moieties. It is possible to recognise the coupling of the analyte to the receptor moiety through the dynamic response of the magnetic nanoparticles to a modulating applied magnetic field. Differences in dynamic response can arise between magnetic nanoparticles which have analytes bound to its receptor moieties and magnetic nanoparticles which do not have the analytes attached. This is because magnetic nanoparticles without analyte present are better able to follow the variation in the applied magnetic field, i.e., they can more quickly align with the magnetic field. Magnetic nanoparticles which are loaded with analytes will have a higher angular momentum and therefore experience more hydrodynamic drag in the sample. In this way, it is possible to discriminate between magnetic nanoparticles of the same kind depending on whether analyte is bound. It is particularly convenient to utilise embodiments in which a permanent magnet is rotated around the sample at one or more desired frequencies. At low frequencies, the magnetic nanoparticles may be able to follow the rotating magnet. However, as the frequency is increased, the magnetic nanoparticles increasingly lag behind the magnetic field (until at some point the magnetic field catches up, giving the magnetic nanoparticles a 'kick'). Therefore, the phase lag of the response of the magnetic nanoparticles with respect to the frequency of the magnetic field constitutes a parameter by which the magnetic nanoparticles may be detected. Magnetic nanoparticles without analytes experience a lower hydrodynamic drag, and are thus better able to follow the changing vector of the magnetic field. This gives rise to characteristic responses in the time domain in relation to the frequency of rotation of the permanent magnets. It is possible to perform a Fourier transformation of the time domain response in order to produce a frequency domain response. This can advantageous in terms of identifying characteristic responses associated with magnetic nanoparticles.

FIG. 3 shows plots which are indicative of the dynamic magneto-optical responses which might be achieved as a function of the rotational frequency of a magnetic field which is rotated around the sample. The inset shows the magneto-optical signal (solid line) at twice the approximately 0.5 Hz magnetic field frequency (dashed line). This response is realised if the magnetic nanoparticles are able to fully follow the rotation of the magnetic field, because the magnetic nanoparticles are aligned fully with the polarised interrogating light twice per revolution of the magnetic field. In the main graph, the magneto-optic signal shown on the ordinate axis is the component of the magneto-optic response which is in phase with the applied magnetic field. It falls with increasing frequency of the applied magnetic field because the hydrodynamic drag increases with angular rotational velocity, but the applied torque remains constant. Both of the responses shown in FIG. 3 will vary depending on whether analytes are bound to the receptors of the magnetic nanoparticles.

It is possible to detect a plurality of analytes present in a sample, e.g. to perform an assay. In these embodiments, different kinds of magnetic nanoparticles are utilised which have different characteristic magneto-optic responses. Different responses can be achieved by way of varying the length of a rod-shaped or otherwise elongate nanoparticle and/or by varying the magnetic susceptibility, for example through the choice of magnetic material. Preferably, both length and magnetic susceptibility are varied. For example, six different responses can be obtained by employing three different lengths of nano-rods fabricated from materials with two different magnetic susceptibilities. Different receptor moieties can be coupled to the different kinds of nano-rods. Such a system opens the possibility of detecting up to six analytes simultaneously. It may be possible to utilise classes of nanoparticles which signal at different wavelengths, thereby providing at least some wavelength discrimination of the different detection elements in a multiple analyte detection system. For example, the system comprising nano-rods of three different lengths with two different magnetic susceptibilities could be designed to produce signalling vectors which signal at three different wavelengths. However, each combination of nano-rod length and magnetic susceptibility will give rise to a different dynamic response, which can also be used to distinguish between the different classes of magnetic nano-particle. As discussed above, a magnetic nanoparticle which is loaded with analytes gives rise to a different dynamic response to one which is not loaded, because it will have a higher angular momentum and thus will experience more hydrodynamic drag. Therefore, it is possible to distinguish between different kinds of magnetic nanoparticle, and also to distinguish from the dynamic response whether a particular kind of magnetic nanoparticle is loaded with analyte.

The dynamic behaviour of gold coated $Fe_2O_3$ magnetic nanorods has been simulated for rods having dimensions such that their optical absorption resulting from plasmonic excitation is well separated to facilitate multi-spectrum diagnosis. The model includes provision for ligand coating and subsequent attachment of antigens. FIG. 4 shows the dynamic behaviour of rods of different lengths, and hence different optical signatures, with and without ligand coatings. More specifically, rods of dimensions 37×19 nm, 50×12 nm and 50×8 nm are considered. These rods can be separately excited at different wavelengths within the visible or near infra-red regions of the electromagnetic spectrum. Broadly speaking, the excitations are in the 400-900 nm range, with the 37×19 nm nanorods being excited at a wavelength in the red/near infra-red region, the 50×12 nm rods being excited in the green region, and the 50×8 nm rods being excited in the blue region. The skilled reader will appreciate that the precise excitation wavelengths will depend on a number of factors, such as the detection medium and the precise nature of the coating, but can be readily determined. It can be seen that their dynamic behaviour is sufficiently different to easily differentiate between rods with 40, 42, 44, and without 46, 48, 50 ligand coatings, and it follows that the behaviour of rods that pick up antigens will be equally affected by the additional drag.

FIG. 4 shows that the particles, which are initially aligned with the field, rotate synchronously with the field but with a phase lag dependent on their individual size and shape etc. This phase lag increases smoothly with frequency up to a critical frequency determined by when it reaches $\pi/2$ radians when the behaviour becomes unstable.

Good separation is observed between the critical frequencies not only between rods of different sizes but also between rods with and without additional mass/drag in the form of ligand and antibody coatings or attachments. The separation between the critical frequencies is such that when operating below these frequencies it will be possible by using phase or time domain analysis of the optical signals to discriminate between rods signalling at a specific wavelength that have picked up antibodies and those that have not.

From this, it is possible to detect a plurality of analytes in a single experiment, such as a single assay. The technique offers the possibility of discriminating between magnetic nanoparticle which are loaded with analytes, and those which are not. This means that it may not be necessary to utilise pre-processing to remove nanoparticles which do not have analytes attached prior to performing an assay.

REFERENCES

1. Anker, J. N; Kopelman, R, Appl. Phys. Lett. 82, 1102 (2003)
2. D. M Newman, J. Heptinstall, R. J. Matelon, et al., Biopyhsical J. 95 (2008) 994-1000.
3. P. F Mens, R. J Matelon, B. Y Nour, et al., Malaria Journal 9 (2010) 207
4. D. M Newman, R. J Matelon, M. L. Wears, L. Savage; IEEE J. Selected Topics in Quantum Electronics 16 (2010) 573-580
5. D. M Newman, R. J Matelon, M. L Wears, L. Savage et al. PhotoicsGlobal@Singapore, 2008. IPGC 2008. IEEE, ISBN: 978-1-4244-3901-0, DOI: 10.1109/IPGC.2008.4781387
6. Lia Stanciu, Yu-Ho Won, Mallikarjunarao Ganesana and Silvana Andreescu, Sensors 2009, 9, 2976-2999
7. Peter Zijlstra, James W. M. Chon & Min Gu, Natures Letters Vol 459 2009, 410-413
8. Jing Zhu, Ken-Tye Yong et al. Nanotechnology 21 (2010) 285106 (8pp)
9. Mona B. Mohamed, Victor Volkov, Stephan Link, Mostafa A. El-Sayed, Chemical Physics Letters 317, 2000, 517-523
10. Pooja M Tiwari, Komal Vig, Vida A Dennis and Shree R Singh, Nanomaterials 1(2011) 31-63.
11. H Y Park, M J Schadt, L Wang, I I S Lim, P N Njoaki, S H Kim, M J Jang, J Luo and C J Zhong, Langmuir 2007, 23, 9050-9056.
12. P Hien, T Thao, C Cao, S J Sim, J. Magn. Magn. Mater. 2008, 320, 2049-2055
13. D Tang, R Yuan, Y Chai, Bioproc. Biosyst. Eng. 2008, 31, 55-61
14. G K Kouassi, P Wang, S Sreevatan, J Irudayaraj, Biotechnol. Progr. 2007, 23, 1239-1244
15. L Liu, H Ding, K T Yong, I Roy, W C Law, A Kopwitthaya, R Kumar, F Erogbogbo, X Zhang, P Prasad, Plasmonics (2011) 6:105-1112

The invention claimed is:

1. A method of detecting a plurality of analytes including the steps of:
   i) providing a sample which contains the analytes and a plurality of different kinds of magnetic nanoparticles, in which the magnetic nanoparticles include a magnetic body portion which acts as a signalling vector and at least one receptor moiety attached to the body portion for binding to the analyte, each of said kinds binding to a different analyte by virtue of having a different receptor moiety;
   ii) applying a magnetic field across at least a portion of the sample to orient the magnetic nanoparticles with respect to the applied magnetic field and varying the direction of the applied magnetic field at a desired frequency;
   iii) introducing polarized electromagnetic radiation into the sample;
   iv) detecting a phase lag between the magnetic nanoparticles and the frequency of the variation of the direction of the applied magnetic field by detecting a physical property which varies in dependence on the orientation of the magnetic nanoparticles with respect to the applied magnetic field, wherein the physical property is associated with the interaction of the electromagnetic radiation with the magnetic body portion which thereby acts as a signalling vector; and
   v) correlating the phase lag with the presence of the analytes in which the phase lag associated with each of said kinds of magnetic nanoparticles when bound to its associated analyte is different, allowing the phase lag to be correlated with the presence of the associated analyte.

2. A method of detecting plurality of analytes according to claim 1 in which the electromagnetic radiation propagates through the sample along an axis which is transverse to the direction of the applied magnetic field.

3. A method according to claim 1 in which the direction of the applied magnetic field is varied by rotating said direction about the sample at a desired rotational frequency.

4. A method according to claim 3 in which the rotational frequency is varied.

5. A method according to claim 4 in which the phase lag is detected as a function of the rotational frequency.

6. A method of detecting a plurality of analytes according to claim 1 in which the electromagnetic radiation is in the range 400 to 2500 nm.

7. A method of detecting a plurality of analytes according to claim 1 in which the plurality of analyte are a biomolecule or biological material.

8. The method of claim 1, wherein the frequency in step (ii) is 50 Hz or less.

9. A method of detecting a plurality of analytes according to claim 1 in which the magnetic body portion includes a magnetic core and a surface coating.

10. A method of detecting a plurality of analytes according to claim 9 in which the surface coating and the electromagnetic radiation interact to produce plasmons, thereby enhancing the detection of the physical property.

11. A method of detecting a plurality of analytes according to claim 9 in which the detected physical property is fluorescence emitted from the surface coating.

12. A method of detecting a plurality of analytes according to claim 9 in which the surface coating is gold.

13. A method of detecting a plurality of analytes including the steps of:
   i) providing a sample which contains the analytes and a plurality of different kinds of magnetic nanoparticles, in which the magnetic nanoparticles include a magnetic body portion which acts as a signalling vector and at least one receptor moiety attached to the body portion for binding to the analyte, each of said kinds binding to a different analyte by virtue of having a different receptor moiety;
   ii) applying a magnetic field across at least a portion of the sample to orient the magnetic nanoparticles with respect to the applied magnetic field and varying the direction of the applied magnetic field by rotating said direction about the sample at a desired rotational frequency;
   iii) introducing polarized electromagnetic radiation into the sample;
   iv) detecting a phase lag between the magnetic nanoparticles and the rotational frequency of the applied magnetic field by detecting a physical property which varies in dependence on the orientation of the magnetic nanoparticles with respect to the applied magnetic field, wherein the physical property is associated with the interaction of the electromagnetic radiation with the magnetic body portion which thereby acts as a signalling vector; and
   v) correlating the detected phase lag with the presence of the analytes in which the phase lag associated with each of said kinds of magnetic nanoparticles when bound to its associated analyte is different, allowing the phase lag to be correlated with the presence of the associated analyte.

14. A method of detecting a plurality of analytes including the steps of:
   i) providing a sample which contains the analytes and a plurality of different kinds of magnetic nanoparticles, in which the magnetic nanoparticles include a magnetic body portion which acts as a signalling vector and at least one receptor moiety attached to the body portion for binding to the analyte, each of said kinds binding to a different analyte by virtue of having a different receptor moiety;
   ii) applying a magnetic field across at least a portion of the sample to orient the magnetic nanoparticles with respect to the applied magnetic field and varying the direction of the applied magnetic field by rotating said direction about the sample at a desired rotational frequency, wherein the rotational frequency is varied;
   iii) introducing polarized electromagnetic radiation into the sample;
   iv) detecting a phase lag between the magnetic nanoparticles and the rotational frequency of the applied magnetic field as a function of the rotational frequency by detecting a physical property which varies in dependence on the orientation of the magnetic nanoparticles with respect to the applied magnetic field, wherein the physical property is associated with the interaction of the electromagnetic radiation with the magnetic body portion which thereby acts as a signalling vector; and
   v) correlating the phase lag with the presence of the analytes in which the phase lag associated with each of said kinds of magnetic nanoparticles when bound to its associated analyte is different, allowing the phase lag to be correlated with the presence of the associated analyte.

15. A method of detecting a plurality of analytes including the steps of:
   i) providing a sample which contains the analytes and a plurality of different kinds of magnetic nanoparticles, in which the magnetic nanoparticles include a magnetic body portion which acts as a signalling vector and at least one receptor moiety attached to the body portion for binding to the analyte, each of said kinds binding to a different analyte by virtue of having a different receptor moiety;
   ii) applying a magnetic field across at least a portion of the sample to orient the magnetic nanoparticles with respect to the applied magnetic field and varying the direction of the applied magnetic field at a frequency of 50 Hz or less;
   iii) introducing electromagnetic radiation into the sample;
   iv) detecting a phase lag between the magnetic nanoparticles and the frequency of the variation of the direction of the applied magnetic field by detecting a physical property which varies in dependence on the orientation of the magnetic nanoparticles with respect to the applied magnetic field, wherein the physical property is associated with the interaction of the electromagnetic radiation with the magnetic body portion which thereby acts as a signalling vector; and
   v) correlating the phase lag with the presence of the analytes in which the phase lag associated with each of said kinds of magnetic nanoparticles when bound to its associated analyte is different, allowing the phase lag to be correlated with the presence of the associated analyte.

* * * * *